United States Patent
Sowden

[11] Patent Number: 5,868,846
[45] Date of Patent: Feb. 9, 1999

[54] VACUUM NOZZLE ASSEMBLY

[75] Inventor: Harry S. Sowden, Glenside, Pa.

[73] Assignee: McNeil-PPC, Inc., Skillman, N.J.

[21] Appl. No.: 915,311

[22] Filed: Aug. 20, 1997

[51] Int. Cl.$^6$ .................. B05C 3/00; A23G 3/24
[52] U.S. Cl. ................. 118/668; 118/30; 118/676
[58] Field of Search ..................... 118/668, 670, 118/30, 676, 16

[56] References Cited

U.S. PATENT DOCUMENTS

| | | | |
|---|---|---|---|
| 499,542 | 6/1893 | Heineman | 264/15 |
| 1,123,934 | 1/1915 | Lorentzen et al. | 18/23 |
| 2,889,801 | 6/1959 | Pikal | 118/16 |
| 2,995,182 | 5/1961 | Hendrickson . | |
| 3,453,989 | 7/1969 | Bippus | 273/276 |
| 3,604,452 | 9/1971 | Daniels et al. | 137/523 |
| 3,773,091 | 11/1973 | Boyd et al. | 141/42 |
| 3,896,762 | 7/1975 | Banker | 118/30 |
| 4,039,482 | 8/1977 | Hoyer et al. | 427/294 |
| 4,510,168 | 4/1985 | Sakashita et al. | 427/3 |
| 4,526,129 | 7/1985 | Braden | 118/503 |
| 4,597,931 | 7/1986 | Watanabe et al. | 264/129 |
| 4,669,416 | 6/1987 | Delgado et al. | 118/503 |
| 4,684,113 | 8/1987 | Douglas et al. | 269/21 |
| 4,694,776 | 9/1987 | Sandbach et al. | 118/500 |
| 4,820,524 | 4/1989 | Berta | 424/474 |
| 4,867,983 | 9/1989 | Berta | 118/503 |
| 4,921,108 | 5/1990 | Berta | 209/625 |
| 4,940,499 | 7/1990 | Lebrun et al. | 156/69 |
| 4,965,089 | 10/1990 | Sauter et al. | 427/3 |
| 4,966,771 | 10/1990 | Berta | 424/478 |
| 4,990,358 | 2/1991 | Berta | 427/3 |
| 5,098,749 | 3/1992 | Gabriel et al. | 427/430.1 |
| 5,228,916 | 7/1993 | Berta | 118/30 |
| 5,234,099 | 8/1993 | Berta | 118/803.1 |
| 5,314,537 | 5/1994 | Berta | 118/30 |
| 5,405,123 | 4/1995 | Mielenz | 269/21 |
| 5,436,026 | 7/1995 | Berta | 427/2.14 |
| 5,466,290 | 11/1995 | Berta | 118/20 |
| 5,498,441 | 3/1996 | Berta | 427/2.14 |
| 5,503,673 | 4/1996 | Berta | 118/16 |
| 5,538,125 | 7/1996 | Berta | 198/345.3 |
| 5,679,406 | 10/1997 | Berta | 427/289 |
| 5,709,536 | 1/1998 | Renfro et al. | 417/383 |

Primary Examiner—Diana Dudash
Attorney, Agent, or Firm—Joseph F. Leightner

[57] ABSTRACT

A nozzle assembly is provided with a valve to enable the coating of low aspect ratio items such as tablets. In a preferred embodiment a valve is disclosed such that the vacuum forces acting on the surfaces of the valve are equal to the weight of the valve. This balancing of the weight of the valve and the vacuum forces allows gravity to be the primary motive force for actuation. The weight of the valve is used to detect a tablet, such that when a tablet is missing, the valve prevents any coating from being pulled into the nozzle.

5 Claims, 6 Drawing Sheets

VACUUM NOZZLE ASSEMBLY

BACKGROUND OF THE INVENTION

The present invention relates to vacuum nozzle assembly, in particular a vacuum nozzle assembly containing a valve assembly.

As disclosed in U.S. Pat. Nos. 5,228,916, 5,538,125 and 5,503,673, machines have been designed to coat pharmaceuticals with agents such as gelatin, to aid in the swallowing of the tablet. In coating the tablet it is desirable to coat the tablet with different colors which aid in identifying the product for both the pharmacist and the consumer. In order to coat both sides of a tablet with different colors it is common practice to invert the tablet from one side to the other in order to apply the different colors.

In commercial practice of coating the tablets, vacuum is used as a means of gripping the tablets as they are coated. Since the vacuum nozzles holding the tablets are just above the coating bath, if a tablet is missing or not properly placed in the holder, the coating solution will be pulled by vacuum into the nozzle. Once the coating solution is pulled by vacuum into the nozzle, the coating solution will solidify either plugging or significantly reducing the vacuum which makes it unlikely that the tablet can be held in place in the next cycle. Once the nozzle is plugged, the coating machine must be shut down and cleaned. Plugged nozzles is a significant cause of downtime and lost production.

One attempt at solving this problem is the use of photo electric eyes which check for missing tablets in the holders. If the electric eye detects a missing tablet the electric eye will shut down the machine so that an operator can manually replace the missing tablet in the machine. This semi-automatic approach is both labor intensive and inefficient.

It would be highly desirable that an automatic device be employed to prevent the vacuuming of coating solution into a tablet nozzle. Preferably the device would also allow the coating machine to remain in continuous operation if a tablet is missing and not require an operator to replace the tablet.

FIELD OF THE INVENTION

A primary object of the present invention is to provide a vacuum holder which can be employed in the coating of objects, particularly objects with low aspect ratios such as tablets, which allows the coating to be dipped while at the same time preventing the coating from being pulled into the nozzle.

Another object of the present invention is to provide a vacuum nozzle assembly which will allow the coating machine to remain in operation if a tablet is missing. With the inclusion of the present invention the coating machine can be operated as an automated machine whereas now the coating machine is operated semi-automatically.

The present invention automatically senses the presence of a tablet and does not require the use of any electronic means to operate.

The present invention relates to a vacuum nozzle apparatus for the coating of a low aspect ratio object comprising: a body with a plurality of apertures, the apertures comprising an enlarged cavity and vacuum passages, said enlarged cavity having a top, bottom and side surfaces; a nozzle extending from the body, the nozzle having an annular chamber with diameter less than the enlarged cavity; the nozzle and enlarged cavity contacting such that a continuous aperture is provided between the enlarged channel, vacuum passage and nozzle; a nozzle detection pin which has a diameter less than the diameter of the nozzle and a length substantially equal or greater than the length of the nozzle; means for sealing the enlarged cavity; said pin attached to the means for sealing the enlarged cavity, and the means for sealing the enlarged cavity free to move in a substantially linear motion within the enlarged cavity contained within the body, wherein in an inverted position the means for sealing the enlarged cavity contacts the top of the enlarged cavity thereby sealing the continuous aperture between the enlarged cavity and nozzle.

The present invention also provides a method for dip coating a low aspect item, such as a tablet which does not require any electrical means to hold the tablet in place or to detect when the tablet is not present. The method comprises the steps of coating a tablet comprising: providing a tablet; attaching the tablet to a nozzle through the use of a vacuum source; inverting the tablet and nozzle into a coating solution; wherein if the low aspect ratio item is not attached to the nozzle when it is inverted the vacuum in the nozzle is shut off.

The present method has the feature wherein the vacuum is turned off through gravity activated mechanical means without the use of electrical means. The method of the present invention also has a feature in which means are provided to detect the absence of the low aspect ratio item in the nozzle. These features allow the coating machine to remain operating even when an item is not in the nozzle thereby providing higher production of coated product.

DETAILED DESCRIPTION OF THE PREFERRED EMBODIMENTS

The invention together with the above and other objects may best be understood from a consideration of the following detailed description of an illustrative embodiment in the course of which reference is made to the accompanying drawings.

DETAILED DESCRIPTION OF THE INVENTION

Figure 1A:
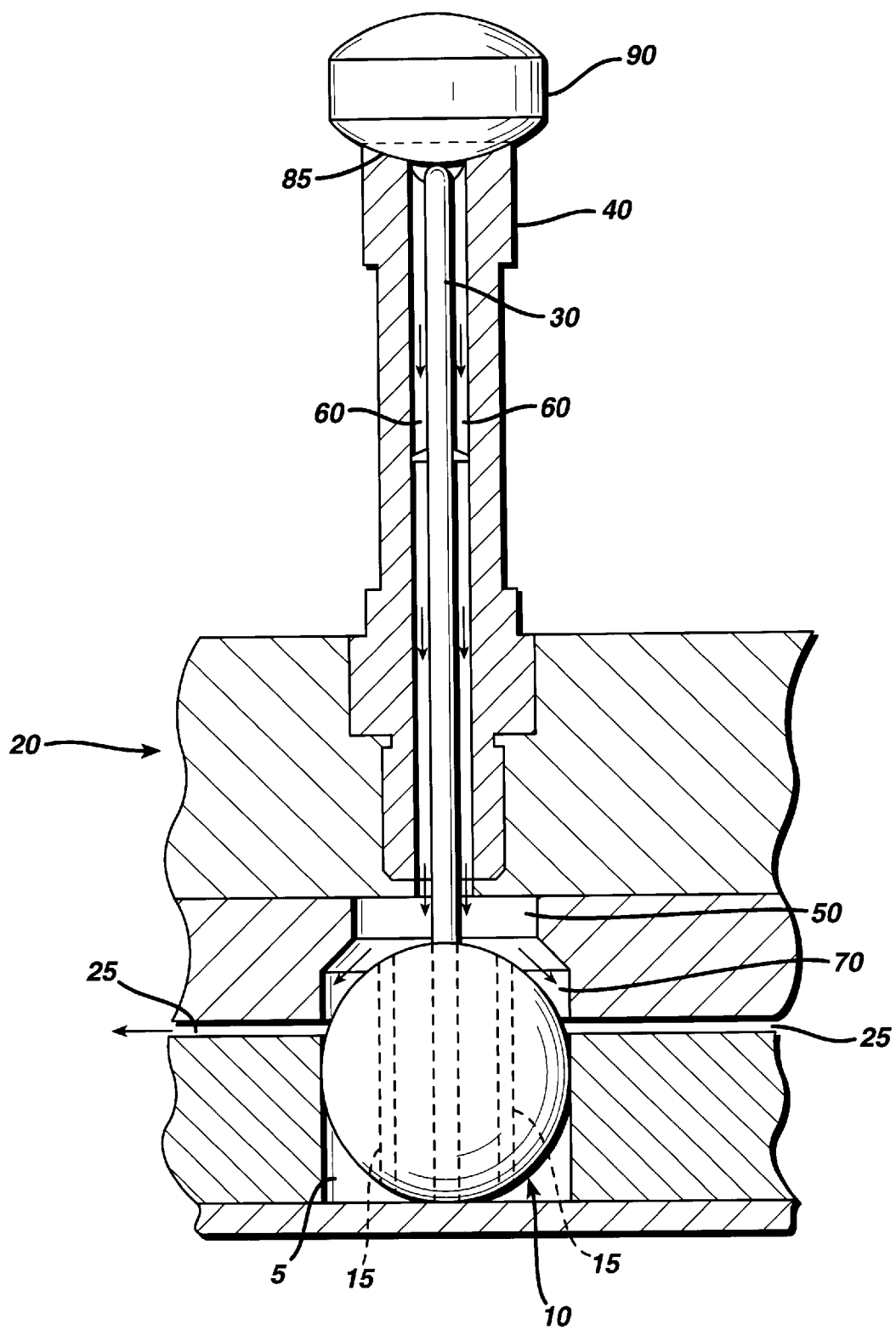
FIG. 1a is a cross-sectional view of the nozzle assembly in the upright position holding a tablet.

Referring to the drawings and first to FIG. 1a, The body of the vacuum assembly 20 is manufactured to accept the nozzle 40. For ease of manufacture and assembly it is preferred that the nozzles are screwed into the body. Within the nozzle is a tablet detection pin 30 which is attached to means for sealing the enlarged cavity 10. In a preferred embodiment the means for sealing the enlarged cavity is shaped as ball. The ball is free to move within an enlarged cavity 5 in a substantially vertical motion. In a highly preferred embodiment, the ball has two or more ball vacuum channels 15 which are provided through the ball in substantially the same direction as the nozzle. The vacuum passage orifices (or slots) 25 are provided substantially perpendicular to the nozzle tube and are connected to a vacuum source (not shown). The vacuum passage orifices are approximately 0.060 inches (0.1524 cm) in diameter. The vacuum passage orifice are in connection with the enlarged cavity such that a channel 70 is created, allowing the vacuum to be provided around the means for sealing the enlarged cavity and nozzle detection pin to flow through the nozzle vacuum channel 60 to the top of the nozzle. In the upright position, the ball does not rest upon the collar 50, thereby providing a vacuum to the nozzle top 85.

As depicted in FIG. 1a, a tablet 90 is provided and the length of the nozzle detection pin in the upright position is lower than the nozzle top 85 which is manufactured to accept the tablet 90. Preferably, the nozzle top 85 is machined with the same radius of curvature to securely receive and hold the tablet.

Figure 1B:
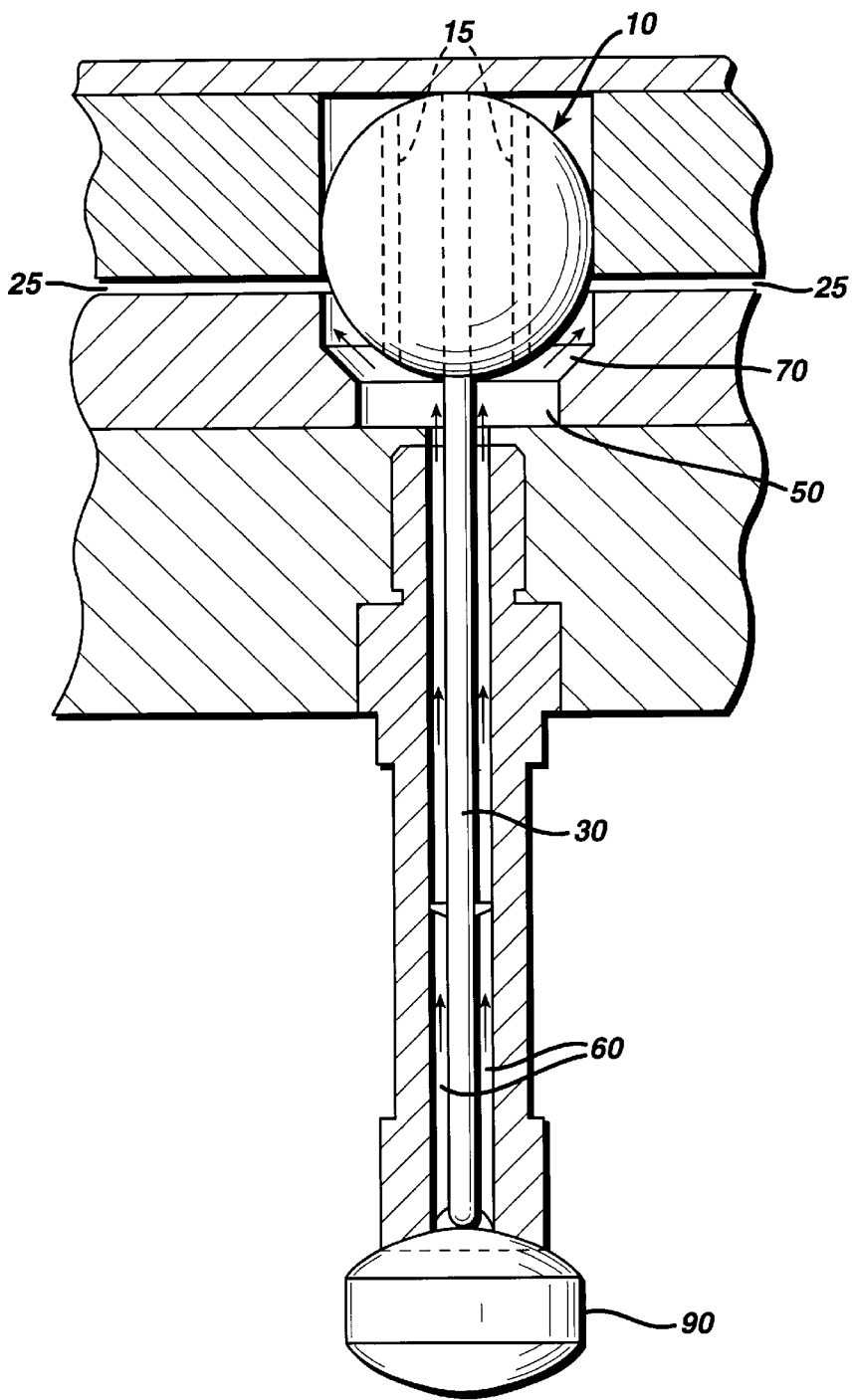
FIG. 1b is a cross-sectional view of the nozzle assembly in an inverted position containing a tablet. As used throughout this specification, inverted is understood to mean that the tablet is being held in the nozzle assembly despite the forces of gravity.

Now referring to FIG. 1b, the nozzle assembly is in the inverted position. With the tablet in position, the ball 10 is in position to keep the vacuum passage open thereby maintaining the tablet in position. The vacuum is equalized in and around the ball such that the ball is suspended within the enlarged passage which keeps the ball above the vacuum passage orifice. The ball is held in equilibrium above the collar 50 thereby allowing the vacuum to be provided to the nozzle vacuum channel 60.

The vacuum allows the tablet to be held in place while being dipped in the coating solution.

Figure 1C:
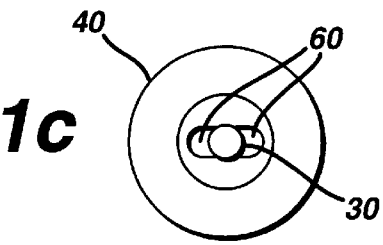
FIG. 1(c) is a cross-sectional view of the nozzle assembly in the upright and inverted position holding a tablet.

FIG. 1c depicts an enlarged view of the nozzle top 85 with the tablet removed for clarity. The nozzle vacuum channels 60 and the nozzle detection pin 30 are visible within the nozzle 40. In a preferred embodiment the nozzle vacuum slots are an oblong orifice with the nozzle detection pin in the center, each of the orifices being approximately 0.0040 inches (0.010 cm).

Figure 2A:
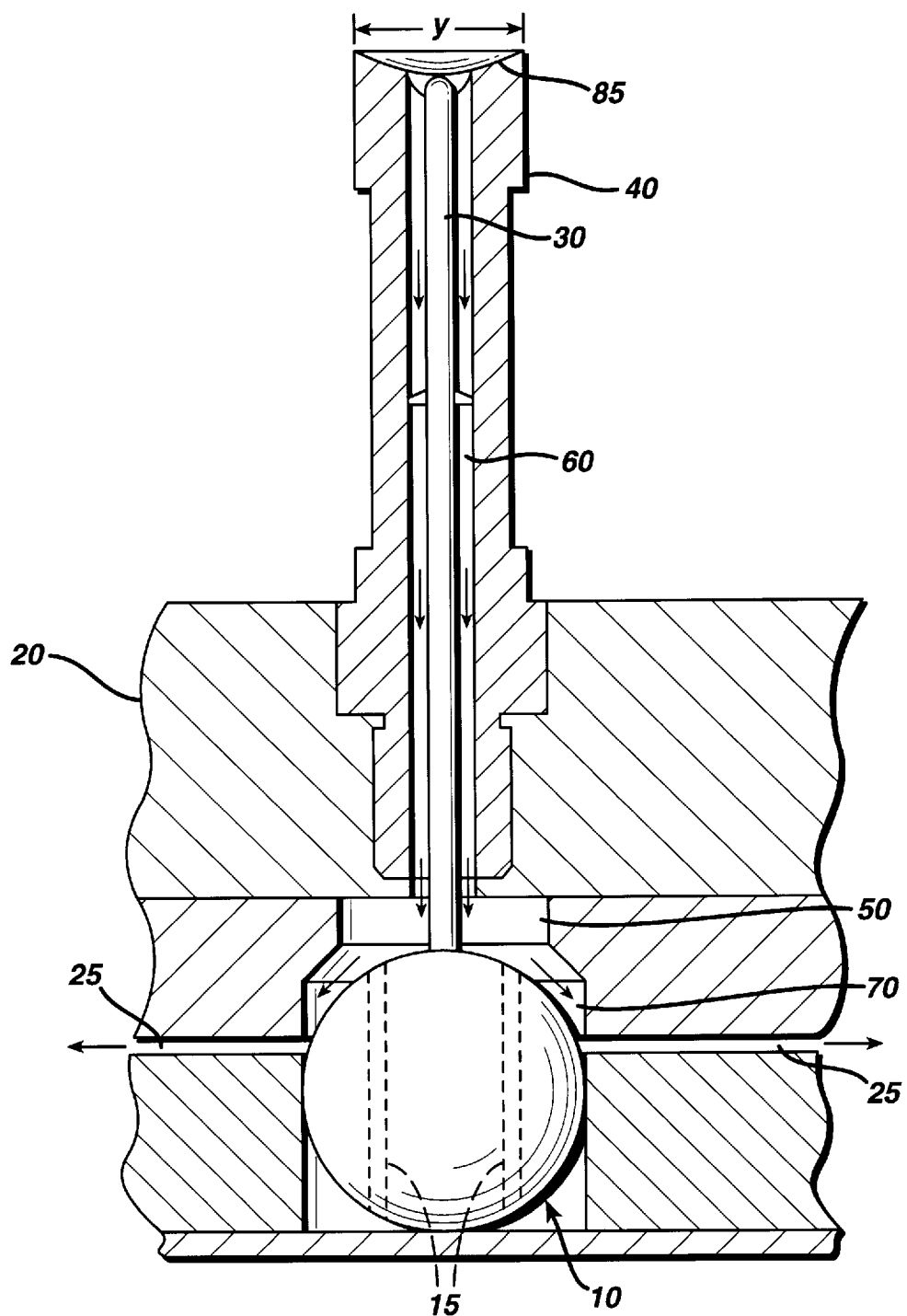
FIGS. 2(a) and 2(b) are cross-sectional views of the nozzle assembly in the upright and inverted positions, respectively, without a tablet.
Figure 2B:
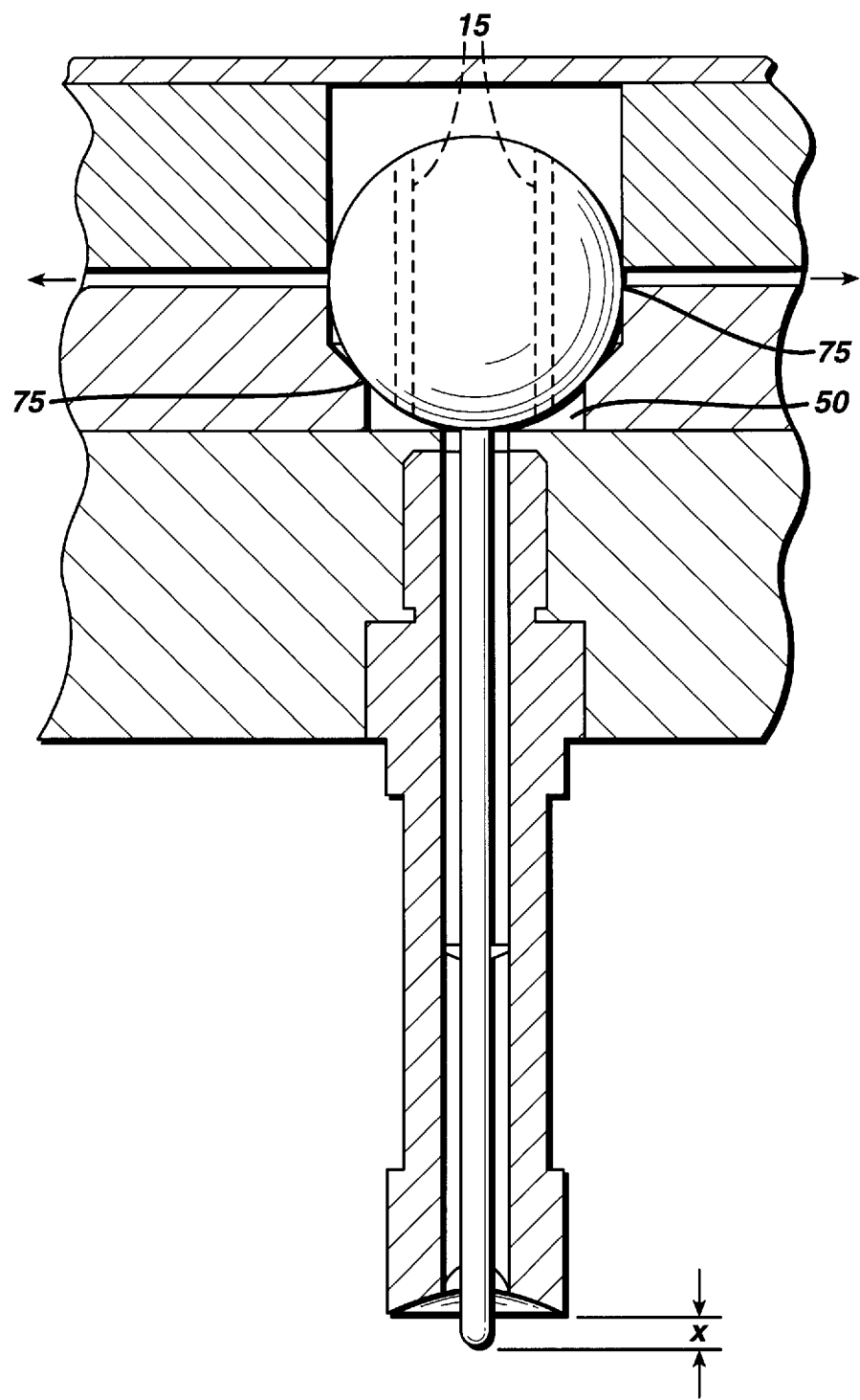

In FIG. 2a, the tablet is not present in the concave end of the nozzle 85, which is designed to accept the object, such as a tablet. The nozzle diameter, y, is preferably the same size as the length of the tablet. In FIG. 2b, the vacuum nozzle is depicted in the inverted position without a tablet. The orifice passages in the ball allow the pressure to equalize the pressure on both sides of the ball, thereby allowing gravity to be the only force acting on the ball 10. The ball now rests on the collar 50 thereby providing a sealing of the vacuum passage at contact points 75. The annular slots being blocked at the sealing points prevents the vacuum from being exerted on the nozzle vacuum channels 60, thereby preventing the coating material to be pulled into the nozzle. As is apparent from the drawing, the nozzle detection pin now protrudes beyond the end of the nozzle by the distance, x. The distance the nozzle detection pin extends beyond the nozzle is not critical but it is desirable that the nozzle detection pin not protrude too far or it may extend into the coating solution. It has been found that the nozzle detection pin which extends approximately 0.0625 inch (0.158 cm) is effective in preventing the coating from being pulled into the nozzle.

When the tablet is not present the vacuum slots equalize the pressure on both sides of the ball from being pulled out of position by the vacuum. The ball is free to make contact with the sealing sides of the body thereby blocking the vacuum passages of the assembly. Those with skill in the art will recognize that other sealing arrangements may be used and the "ball" geometry may be replaced with other shapes and geometries including a cylindrical spool valve. The valve design operates because all of the vacuum forces are equalized through the vent holes and are self canceling. Gravity therefore becomes the only force available to move the ball from the open to closed position. The weight of the ball must be less than that of the vacuum force holding the tablet to the nozzle. If the weight of the ball is more than the vacuum force, the tablets will be knocked off the nozzle by the nozzle detection pin. Therefore the weight of ball 10 and the nozzle vacuum channel 60 must be appropriately chosen so as to balance the vacuum force and gravitational forces so as to maintain the tablet in the inverted position. In a preferred embodiment of the present invention the weight of the ball is approximately 0.0184 pounds (8.35 grams).

Figure 3:
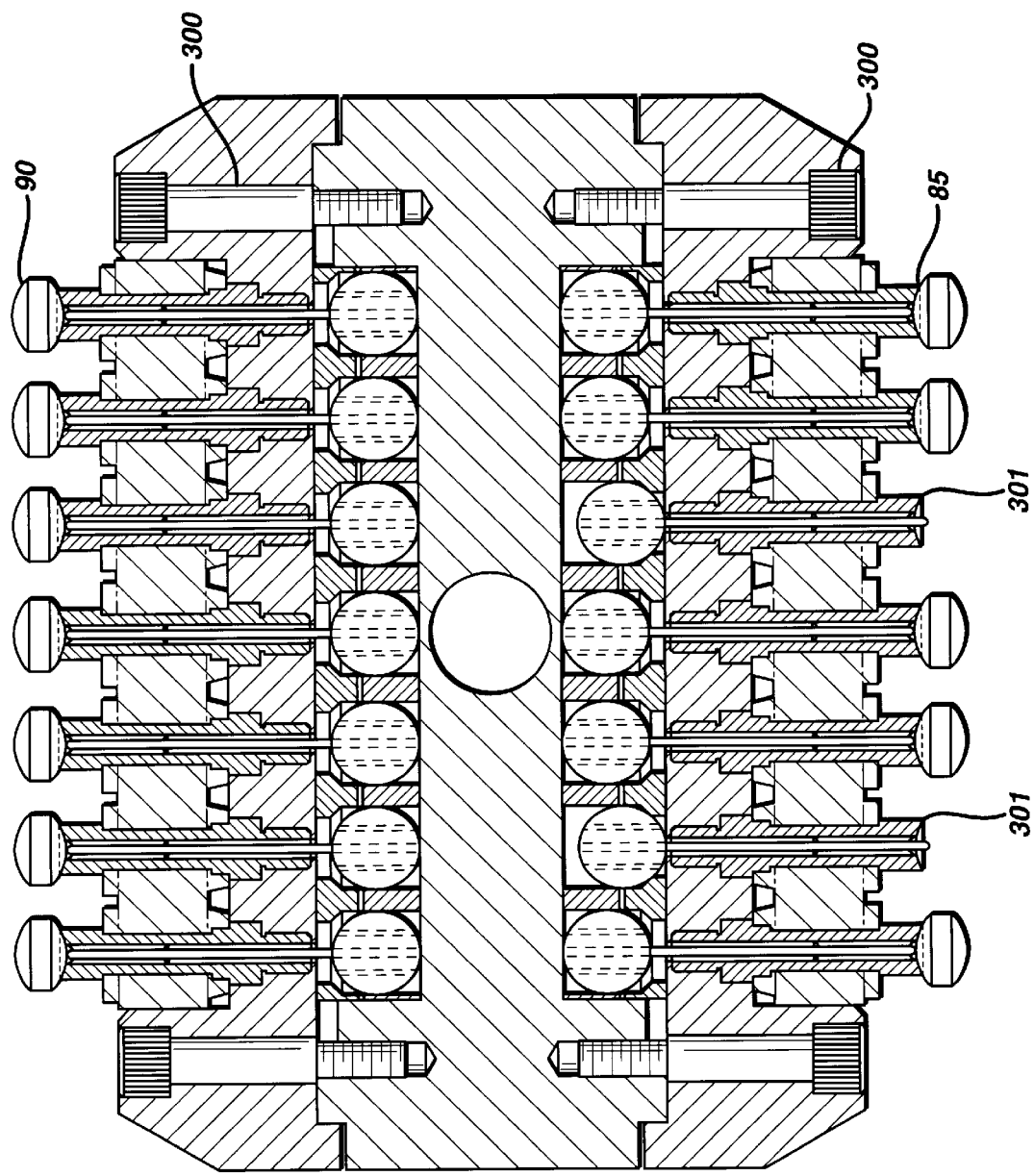
FIG. 3 is a sectional side view of the nozzle manifold assembly containing a plurality of nozzle assemblies. Most of the nozzle assemblies are holding a tablet, some of the nozzle assemblies are not holding a tablet.

FIG. 3 depicts a manifold of the vacuum assembly demonstrating the relative position of the ball and the nozzle detection pins relative to one another depending whether a tablet 90 has been positioned in the nozzle top 85. The nozzle detection pins are depicted extending beyond the end of the nozzle 301. Fastening devices 300 are used to secure the nozzle assemblies to the coating machine. For clarity, the other elements found in FIGS. 1 and 2 are not numbered.

Figure 4A:
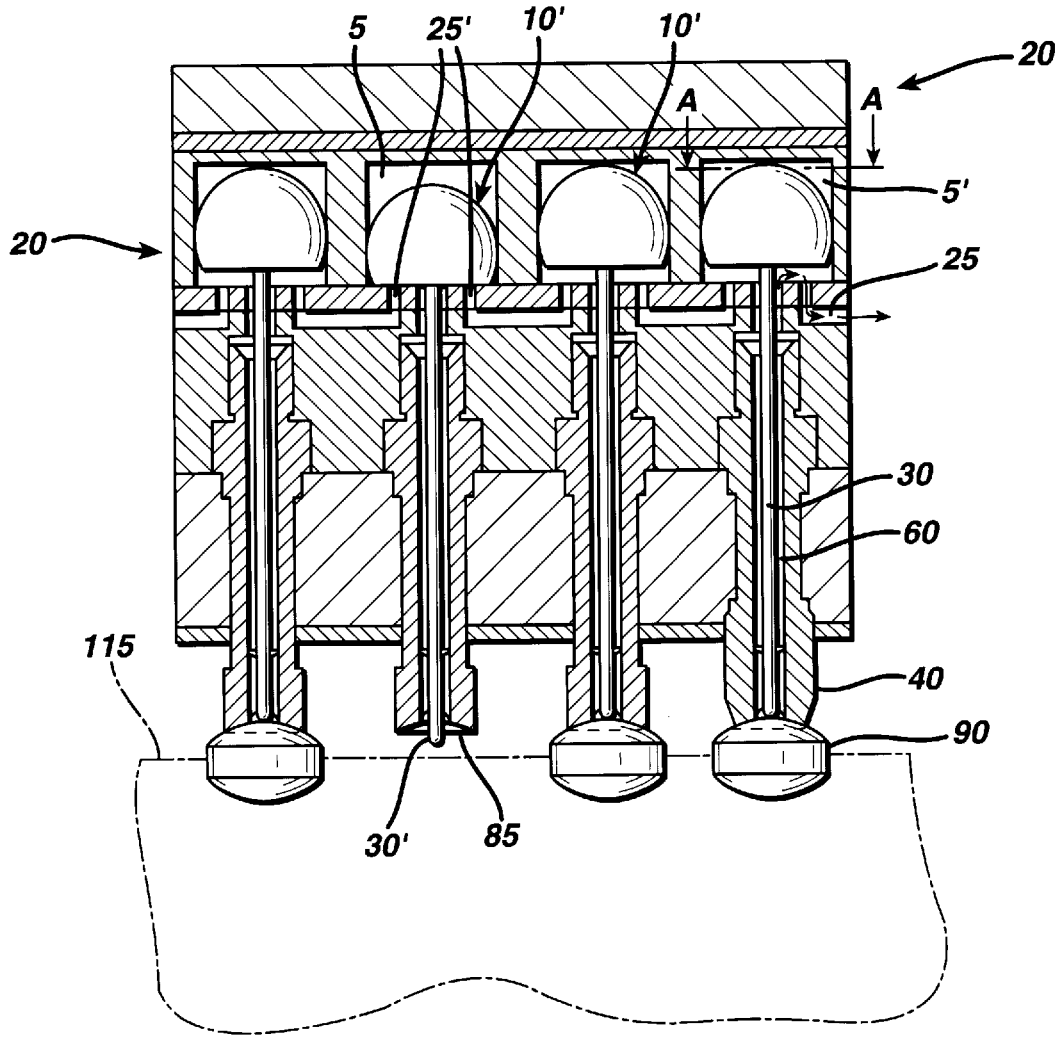
FIG. 4(a) is a cross-sectional view of another embodiment of the nozzle assembly in the inverted position depicting the nozzle assemblies holding tablets, with one nozzle assembly not having a tablet.

In a second embodiment of the invention depicted in FIG. 4(a), the means for sealing the enlarged cavity (previously depicted as a ball in the earlier Figures) does not contain vacuum channels. In this embodiment of the invention, the vacuum passage orifice 25 are provided into an enlarged cavity 5 in which a sealing means 10' is allowed movement in a substantially vertical motion. A vacuum source (not shown) exerts a vacuum on the vacuum passage 25. When a tablet 90 is present the nozzle vacuum passage channel 60 is closed, thereby maintaining the sealing means 10' free to move within the enlarged cavity 5.

When a tablet is not present, as demonstrated in the second nozzle assembly from the left, the nozzle vacuum channel 60 is open to the atmosphere and the nozzle detection pin 30 is free to extend beyond the nozzle top 85. Because the tablet is not present, there is nothing to hold the sealing means 10' in place thereby allowing the sealing means 10' to contact the body of the vacuum assembly 20 effectively closing the vacuum passage orifices 25 at the end of the enlarged cavity. The sealing means 10' thereby provides a seal for the vacuum passage 25' preventing the vacuum forces from pulling the coating material into the nozzle. In a preferred embodiment the nozzle detection pin is allowed to extend beyond the nozzle end but remain above the level of the coating solution 115. The tablets 90 are dipped at the appropriate level in the coating solution.

The second embodiment as depicted in FIG. 4 is not "vacuum neutral". In this embodiment, no orifices or slots are placed in the sealing means to balance the vacuum forces. In this embodiment, the vacuum forces across the sealing means are not self canceling. The sealing means will contact and remain against the vacuum assembly until the vacuum source is shut off. However, it is necessary to shut off the vacuum source at the completion of the coating cycle to remove the coated tablet and to allow the nozzle detection pins to drop to the bottom of the enlarged cavity 5'. The second embodiment depicted in FIG. 4, requires that the vacuum is shut off by an automatic remote valve, such as a solenoid activated valve (not shown), when the vacuum nozzle assembly is in the upright position at the beginning of each cycle in which a tablet is paced on the nozzle top 85.

Figure 4B:
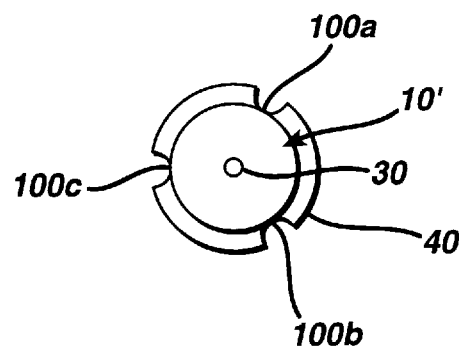
FIG. 4b is a view of the nozzle tube, vacuum slots and nozzle detection pin depicted in section A—A.

The non-vacuum neutral embodiment is more tolerant of dust and other particulate matter due to the 3 point contact (100a, 10b, 100c as depicted in FIG. 4b) against the walls of the enlarged cavity 5 and large clearances it affords and the more positive shut-off action.

FIG. 4b is a view of the needle detection valve pin 30, sealing means 10' from above. The area of three point contact are denoted as 100a, 100b and 100c. The nozzle body 40 surrounds each of the sealing means 10'.

The nozzle assemblies of the present invention can be constructed to provide as many individual nozzles in any pattern as may be required to hold the objects in place while inverted. Large numbers of vacuum assemblies can be provided to accommodate items that require large numbers of items be dipped at a time, such as tablets or capsules. The present invention may also be used to coat other items one at time as may be necessary.

The vacuum nozzle of the present invention is preferably assembled from several pieces and joined together using appropriate fasteners. A preferred manner in which the vacuum nozzle assembly is formed is to have the nozzle attached to the body by a threaded connection. In an embodiment of the invention which is easy to fabricate and assembly, the body is comprised of three sections, a top section in which the nozzles are attached, a middle section in which forms the seal when the sealing means is in contact with it and a bottom section in which contains a plurality of cavities in which the sealing means are contained and are free to move in a substantially linear direction. The three sections of the body may be held in proper alignment by positioning means, such as pins and held in place through the use of fasteners, such as screws.

The nozzle assemble of the present invention is not limited by the materials of construction. The nozzle assembly should be constructed from materials suitable for the coating environment. Such materials include stainless steel, aluminum, steel, alloys, polymers and combinations of these materials. Most preferred are assemblies constructed of aluminum and stainless steel.

While the present invention has been described with reference to low aspect ratio objects and in particular a tablet, the present invention can also be used to dip coat other objects, preferably those with low aspect ratios including but not limited to, capsules, pills, and vitamins. As used throughout low aspect ratio object is understood to mean an object in which its length is greater than about one and half times the height of the object.

What is claimed is:

1. A vacuum nozzle apparatus for the coating of a low aspect ratio objects comprising: a body with a plurality of apertures, the apertures comprising an enlarged cavity and vacuum passages, said enlarged cavity having a top, bottom and side surfaces, and a collar integral with the top surface; a plurality of nozzles extending from the body at said collar, each nozzle having an annular chamber with diameter less than the enlarged cavity contacting such that a continuous aperture is provided between the enlarged channel, vacuum passages and nozzle; a nozzle detection pin which has a diameter less than the diameter of the nozzle and a length substantially equal or greater than the length of the nozzle; means for sealing the enlarged cavity; said pin attached to the means for sealing the enlarged cavity free to move in a substantially linear motion within the enlarged cavity contained within the body, wherein in an inverted position the means for sealing the enlarged cavity contacts the top of the enlarged cavity thereby sealing the continuous aperture between the enlarged cavity and nozzle.

2. The apparatus of claim 1 wherein the means for sealing the enlarged cavity is provided with at least two vacuum channels.

3. The apparatus of claim 2 wherein the means for sealing the enlarged cavity is substantially spherical in shape.

4. The apparatus of claim 1 wherein the means for detecting the tablet extends beyond the nozzle when the means for sealing the enlarged cavity contacts the collar.

5. The apparatus of claim 1 wherein the annular chamber is substantially perpendicular to the enlarged cavity.

\* \* \* \* \*